United States Patent [19]

Kao et al.

[11] 4,231,937
[45] Nov. 4, 1980

[54] PREPARATION OF ALKYLENE CARBONATES FROM ALKYLENE IODOHYDRINS

[75] Inventors: Jar-lin Kao; Ming N. Sheng, both of Cherry Hill, N.J.

[73] Assignee: Atlantic Richfield Company, Los Angeles, Calif.

[21] Appl. No.: 937,294

[22] Filed: Aug. 28, 1978

[51] Int. Cl.³ .................. C07D 317/36; C07D 317/38
[52] U.S. Cl. ................................................. 260/340.2
[58] Field of Search ....................................... 260/340.2

[56] References Cited

U.S. PATENT DOCUMENTS

| | | | |
|---|---|---|---|
| 3,548,012 | 12/1970 | Cornforth | 260/348.21 |
| 4,009,183 | 2/1977 | Fumagalli et al. | 260/340.2 |

FOREIGN PATENT DOCUMENTS 1169459  5/1964  Fed. Rep. of Germany ........ 260/340.2

OTHER PUBLICATIONS

J. W. Cornforth et al., J. Chem. Soc. (C) (1970) pp. 846–849.

*Primary Examiner*—Norma S. Milestone
*Attorney, Agent, or Firm*—Delbert E. McCaslin

[57] ABSTRACT

A process for the preparation of alkylene carbonates having from 3 to 31 carbon atoms per molecule of the general formula

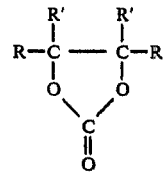

which comprises reacting in the liquid phase the corresponding alkylene iodohydrin having from 2 to 30 carbon atoms per molecule with carbon dioxide in the presence of oxygen or an oxygen-containing gas and an effective amount of a catalytic mixture of (1) an iodide of the metals selected from groups IA, IB, IIA, IIB and VIII of the Periodic Table of Elements and (2) a carbonate of the metals selected from the groups IB, IIA, and IIB of the Periodic Table of Elements, at a temperature of from 30° C. to 120° C., and at a total carbon dioxide and oxygen pressure between about atmospheric and 1400 psig, at a pH value of between 3 and 10.

14 Claims, No Drawings

PREPARATION OF ALKYLENE CARBONATES FROM ALKYLENE IODOHYDRINS

BACKGROUND OF THE INVENTION

A number of prior art processes have been proposed for the preparation of alkylene carbonates, especially ethylene and propylene carbonates. Such methods consist of, e.g., direct preparation from an olefin, catalytic conversion of epoxides with carbon dioxide at high temperatures, and reacting halohydrins with carbon dioxide and alkaline carbonates or bicarbonates.

The present invention is directed to an improved process for the liquid phase preparation of an alkylene carbonate, such as propylene carbonate, in high yield and avoiding problems associated with the prior art processes. More particularly, the present process relates to the synthesis of alkylene carbonates by reacting the corresponding alkylene iodohydrin in a solvent reaction medium with carbon dioxide under elevated temperature and pressure conditions in the presence of oxygen or an oxygen-containing gas and an effective amount of a catalytic mixture of (1) an iodide of the metals selected from group IA, IB, IIA, IIB and VIII metals of the Periodic Table of Elements and (2) a carbonate of the metals selected from group IB, IIA and IIB metals of the Periodic Table of Elements, at a pH value of between about 3 and 10.

U.S. Pat. No. 2,766,258 discloses a method for the preparation of ethylene and propylene carbonate by reacting a chlorohydrin with a stoichiometric amount of a carbonate, bicarbonate or sesquicarbonate under a pressure of carbon dioxide.

U.S. Pat. No. 2,773,070 describes a process for the preparation of alkylene carbonates by treating at elevated temperature and pressure conditions an alkylene oxide with a molar excess of carbon dioxide in the presence of a quaternary ammonium halide.

U.S. Pat. No. 2,784,201 discloses a process for making alkylene carbonates by heating a stoichiometric amount of an alkali metal lower alkyl carbonate with a lower alpha, beta-alkylene chlorohydrin and distilling an alkanol from the reaction mixture.

U.S. Pat. No. 2,873,282 discloses the preparation of alkylene carbonates by reacting an alkylene oxide with carbon dioxide in the presence of a quaternary ammonium hydroxide, carbonate, bicarbonate or ion-exchange resin having quaternary ammonium groups.

U.S. Pat. No. 3,923,842 describes a method for the preparation of cyclic carbonate esters by reacting the corresponding vicinal halohydrin with carbon dioxide in the presence of a stoichiometric amount of an amine compound, such as diethylamine.

The direct preparation of alkylene carbonates including by-product halohydrins from olefins is described in U.S. Pat. No. 4,009,183 employing carbon dioxide and oxygen in the presence of a catalytic system consisting of (a) iodine, metal iodides including alkali and alkaline earth metal iodides and iodohydrines of the olefin and (b) an oxygen carrier selected from manganese dioxide, nitrites, nitrates, nitrogen oxides and a cobalt complex. In addition to substantial amounts of halohydrins being produced as by-product, the carboxylation reaction rate is slow.

The alkylene carbonate products obtained by the process of this invention have known commercial applications, particularly as reactants for the preparation of alkylene oxides such as propylene oxide by decomposition of the carbonate and as organic polymer fiber-forming resin solvents.

A particular feature of the invention in addition to the catalyst system, is the employment of alkylene iodohydrins in conjunction with oxygen in the reaction to oxidize the hydrogen iodide, produced by the reaction with carbon dioxide, to iodine and water thus shifting the equilibrium reaction to the right to completion in favor of the alkylene carbonate in accordance with the following:

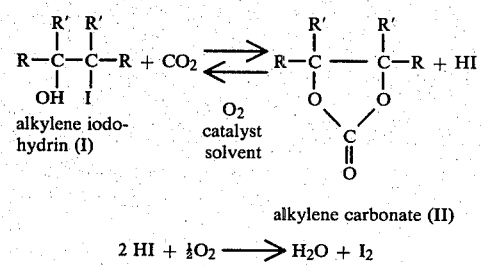

alkylene carbonate (II)

wherein R and R' are as hereinafter defined. The catalyst system in addition to providing a faster rate of reaction and selectivity to the alkylene carbonate than prior art processes also provides, with the use of the metal carbonate salt, the necessary buffer to control the pH of reaction medium within the desired range.

SUMMARY OF THE INVENTION

In accordance with the present invention, there is provided an improved catalytic process for the liquid phase carboxylation of an alkylene iodohydrin to the corresponding alkylene carbonate by reacting the iodohydrin with carbon dioxide in a suitable solvent in the presence of oxygen or an oxygen-containing gas and a catalytic amount of (1) a metal iodide and (2) a metal carbonate at a temperature of from about 30° C. to 120° C. and a total pressure between about atmospheric and 1400 psig and at a pH value of between 3 and 10.

It is an object of this invention to provide an improved process for the preparation of alkylene carbonates, especially ethylene and propylene carbonate, in high yield and selectivity while avoiding operational problems associated with prior art processes.

It is another object of this invention to provide a novel reaction system for the carboxylation of alkylene iodohydrins in the presence of oxygen to the corresponding alkylene carbonate.

It is a further object of this invention to provide a specific catalytic mechanism for the employment of metal iodide and metal carbonate salts in the liquid phase preparation of alkylene carbonates from iodohydrins.

These and other objects and advantages of this invention will become apparent from the description of the invention which follows and from the claims.

DESCRIPTION OF THE INVENTION

In accordance with the present invention, an alkylene carbonate having from 3 to 31 carbon atoms per molecule of the general formula (II) indicated hereinabove, is produced by reacting, under liquid phase conditions, the corresponding alkylene iodohydrin having from 2 to 30 carbon atoms per molecule of the general formula (I) indicated hereinabove, wherein R and R' is individually selected from the group consisting of alkyl groups having from 1 to 8 carbon atoms and aryl or lower (1 to 4 carbon atoms) alkyl, nitro, lower (1 to 4 carbon atoms) alkoxy or halo substituted aryl groups with carbon dioxide, at suitable temperature, pressure and pH conditions, in the presence of oxygen or an oxygen-containing gas such as air, and an effective amount, generally between about 1 and 95 mole percent and preferably between about 10 and 50 mole percent of the iodohydrin employed, of a catalytic mixture consisting of (1) an iodide of a metal selected from groups IA, IB, IIA, IIB and VIII of the Periodic Table of Elements, and (2) a carbonate of a metal selected from groups IIA, IB and IIB of the Periodic Table of Elements.

The reaction between the alkylene iodohydrin and carbon dioxide, as well as the oxidation of the hydrogen iodide produced by the reaction along with the alkylene carbonate, may be carried out in an autoclave or any other pressure reactor. Although the order of addition of reactants and the components forming the catalyst mixture may vary, a general procedure is to charge the iodohydrin, solvent, iodide salt and carbonate salt into the reaction vessel, then introduce the proper amount of carbon dioxide and oxygen to the desired reaction pressure and then heat the mixture to the desired temperature for the appropriate period. The reaction can be carried out batchwise or as a continuous process and the order of addition of the reactants may also be varied to suit the particular apparatus employed. The reaction products are recovered and treated by any conventional method such as distillation, solvent extraction and/or filtration, etc. to effect separation of the alkylene carbonate from unreacted materials, catalyst, by-products, etc.

The alkylene iodohydrins which may be employed in the process of this invention are known in the art and may be prepared for example by the methods described in U.S. Pat. No. 3,923,842 noted hereinabove as well as an article by J. W. Cornforth and D. T. Green, Journ. Chem. Society, Section C., Organic Chemistry, 1970, pp. 846–849. Generally the iodohydrins are employed in concentrations of from about 1 to 30 weight percent and preferably between about 10 and 20 weight percent of the reaction mixture. Representative alkylene iodohydrins suitable for use in the process of this invention include for example, 1-iodo-2-ethanol, 1-iodo-2-propanol, 2-iodo-1-propanol, 1-iodo-2-butanol, 2-iodo-1-butanol, 2-iodo-3-butanol, 1-iodo-2-octanol, 2-iodo-1-octanol, cis-1-iodo-2-cyclohexanol, 2-iodo-1-p-nitrophenylethanol, 2-iodo-1-o-ethoxyphenylpropanol, 1-iodo-2-p-chlorophenylbutanol, 2-iodo-1-p-bromophenylethanol, etc. Mixtures of the iodohydrins may be employed especially, for example, isomeric compounds such as 1-iodo-2-propanol and 2-iodo-1-propanol.

The metal iodides employed in the catalyst component mixture in at least catalytic quantities and suitable for use in the process of this invention include for example, lithium iodide, sodium iodide, potassium iodide, magnesium, calcium, and barium iodides, cuprous, zinc and cadmium iodides, iron, nickel, cobalt, ruthenium, platinum and osmium iodides, etc. The iodides may be employed as part of the catalyst system in the reaction in amounts of from about 0.5 to 48 mole percent and preferably from about 5 to 25 mole percent of the iodohydrin employed.

The metal carbonates employed in the catalyst component mixture in amounts of from about 0.5 to 48 mole percent, preferably from about 5 to 25 mole percent of the iodohydrin employed, and suitable for use in the process of this invention include for example, cupric carbonate dihydroxide, calcium, cadmium, magnesium, strontium, barium and zinc carbonates, etc.

The iodide or carbonate compounds employed may be in a homogeneous state in the reaction mixture at reaction conditions. Thus, the compounds may be present in solution, or suspension. The compounds may be partially or completely soluble under reaction conditions.

Solvents suitable for use in the process of this invention to form the reaction medium are water or mixtures of water with organic solvents miscible with water. Suitable organic solvents include for example, acetonitrile, tertiary butyl alcohol, dimethyl formamide, dioxane, sulfolane, tetrahydrofuran, etc. The ratio of water to organic solvent employed may vary between about 10:1 and 1:10 and preferably between about 5:1 and 1:5.

As indicated above the reaction can be suitably performed by introducing the carbon dioxide and oxygen at desired pressures into contact with the iodohydrin-solvent-catalyst mixture, consisting of the iodide and carbonate metal salt compounds, and heating to the desired temperature. In general, a carbon dioxide pressure of about atmospheric to about 1000 psig partial pressure and preferably from 100 psig to about 700 psig is employed. Liquid carbon dioxide at 800 psig may be used. Higher pressures may be employed but are avoided since there is no apparent economic improvement. Stoichiometric quantities of carbon dioxide are generally employed. However, an excess of $CO_2$ may be employed, for example, in continuous processes where large excess or high carbon dioxide requirements are generally utilized.

At least stoichiometric amounts of oxygen, and generally an excess is employed, and may be in the form of an oxygen-containing gas such as air or oxygen diluted with an inert gas such as nitrogen, etc. The oxygen pressure employed in the process of this invention may be between about atmospheric pressure and 400 psig partial pressure and preferably between about 50 psig and 200 psig.

In order to obtain good selectivity to the alkylene carbonate the reaction medium must not be too low, i.e., lower than 3. In general the process is carried out at a pH value of between 3 and 10 and preferably between about 4 and 7.

The reaction will proceed at temperatures of from about 30° C. to 120° C. It is generally preferred to operate the process at temperatures in the range of 70° C. to 100° C. to obtain the most convenient rate of reaction. Heating and/or cooling means may be employed interior and/or exterior of the reaction to maintain the temperature within the desired range.

The following Examples are provided to illustrate the invention in accordance with the principles of this invention but are not construed as limiting the invention in any way except as indicated by the appended claims.

In the Examples which follow the reactions were run in a 500 ml stainless steel stirred autoclave pressurized with the desired carbon dioxide-oxygen pressure and heated to the desired temperature for 4 hours. After cooling the reaction mixture to 20° C. the pressure was slowly vented. Solids were removed from the liquid product phase and the liquid product analyzed by gas liquid chromatograph to determine alkylene carbonate content and iodohydrin conversion. Iodine content was determined by iodometric titration.

EXAMPLE 1

6.16 g. cupric carbonate dihydroxide, 4.62 g. potassium iodide, 15.61 g. propylene iodohydrin mixed isomers (86 mole percent 1-iodo-2-propanol and 14 mol percent 2-iodo-1-propanol), 30 ml. acetonitrile, 120 ml. water was charged to the autoclave which was then pressurized with 600 psig carbon dioxide and 200 psig oxygen. The reaction was run with stirring at 100° C. for a period of 4 hours. After cooling to 20° C. the pressure was vented and the liquid reaction product filtered to remove solids. Gas liquid chromatographic analysis showed an 84 mole percent selectivity to propylene carbonate at 75 mole percent propylene iodohydrin conversion in addition to by-product propylene oxide (3 percent), propanal (4 percent) and acetone (7 percent). Based on the propylene iodohydrin conversion a 75 mole percent yield of iodine was determined by iodometric titration.

EXAMPLES 2 to 9

In Examples 2 to 9, which follow in Table form, the procedure and general operating conditions as employed in Example 1 was repeated using various catalytic mixtures of metal iodides and metal carbonates along with the propylene iodohydrin isomeric mixture. The catalytic mixtures employed and experimental results in mole percent propylene iodohydrin conversion, propylene carbonate selectivity and iodine yield are set forth in Table 1 as determined by gas liquid chromatographic and iodometric titration analysis.

TABLE 1

| Ex. No. | Catalyst (gms.) | Mole % Conversion | Mole % Selectivity | Mole % Iodine |
|---|---|---|---|---|
| 2 | KI-4.62 g. CaCO$_3$-2.80 g. | 65 | 75 | 95 |
| 3 | NaI-4.17 g. CuCO$_3$ . Cu(OH)$_2$-6.16 g. | 71 | 84 | 75 |
| 4 | LiI-3.73 g. CuCO$_3$ . Cu(OH)$_2$-6.16 g. | 72 | 83 | 75 |
| 5 | CdI$_2$-5.10 g. CaCO$_3$-11.14 g. | 60 | 62 | 93 |
| 6 | CaI$_2$-4.09 g. ZnCO$_3$-7.00 g. | 70 | 82 | 94 |
| 7 | FeI$_2$-4.30 g. CaCO$_3$-11.14 g. | 60 | 63 | 91 |
| 8 | PdI$_2$-3.60 g. CaCO$_3$-6.16 g. | 71 | 84 | 88 |
| 9 | CuI-4.35 g. CuCO$_3$ . Cu(OH)$_2$-6.16 g. | 74 | 85 | 75 |

EXAMPLES 10 to 12

In Examples 10 to 12 the procedure and general operating conditions as employed in Example 1 was repeated, using the propylene iodohydrin isomeric mixture, except that the concentration of a potassium iodide and cupric carbonate dihydroxide catalyst mixture was varied. The experimental results are shown in Table 2.

TABLE 2

| Ex. No. | Catalyst (gms.) KI | Catalyst (gms.) CuCO$_3$ . Cu(OH)$_2$ | Mole % Conversion | Mole % Selectivity | Mole % Iodine |
|---|---|---|---|---|---|
| 10 | 9.24 | 12.31 | 77 | 84 | 75 |
| 11 | 4.62 | 6.16 | 75 | 84 | 75 |
| 12 | 2.31 | 3.08 | 50 | 53 | 76 |

EXAMPLES 13–14

In Examples 13 and 14 the procedure of Example 1 was repeated employing the propylene isomeric mixture, catalyst mixture, organic solvent and water in the same proportion with a variation of reaction temperature. The experimental results are set forth in Table 3.

TABLE 3

| Ex. No. | Temp. °C. | Mole % Iodohydrin Conversion | Mole % Carbonate Selectivity | Mole % Propylene Glycol By-Product |
|---|---|---|---|---|
| 13 | 70 | 50 | 90 | None |
| 14 | 120* | 99 | 54 | 34 |

*at temperatures of 120° C. and above, the solvolysis of iodohydrins and the hydrolysis of the carbonate occurs to a substantial extent to give the glycol.

EXAMPLES 15 to 17

In Examples 15 to 17 the procedure of Example 1 was repeated employing the same including the amounts of, catalyst charge, organic solvent, water carbon dioxide and oxygen pressure at 100° C. for 4 hours with various alkylene iodohydrins. The results are shown in Table 4.

TABLE 4

| Ex. No. | Iodohydrin | Mole % Iodohydrin Conversion | Mole % Carbonate Selectivity | Mole % Iodine |
|---|---|---|---|---|
| 15 | ethylene iodohydrin | 80 | 88 | 76 |
| 16 | 1-iodo-2-hexanol | 78 | 86 | 74 |
| 17 | 2-iodo-1-phenylethanol | 72 | 84 | 75 |

EXAMPLES 18–19

In Examples 18 and 19 the procedure of Example 1 was repeated using the same, including the amounts of, catalyst mixture, organic solvent, water, carbon dioxide and oxygen pressure at 100° C. for a 4 hour reaction period with a 10:1 isomeric mixture of 1-chloro-2-propanol and 2-chloro-1-propanol and an 8:1 isomeric mixture of 1-bromo-2-propanol and 2-bromo-1-propanol respectively. The results showing low conversion of the halohydrin and low selectivity to the propylene carbonate are set forth in Table 5. Oxygen does not oxidize resulting HCl and HBr produced by the reaction.

TABLE 5

| Ex. No. | Halohydrin | Mole % Halohydrin Conversion | Mole % Carbonate Selectivity |
|---|---|---|---|
| 18 | propylene chlorohydrin | 10% | 58% |
| 19 | propylene bromohydrin | 14% | 61% |

We claim:
1. A process for the preparation of alkylene carbonates having from 3 to 31 carbon atoms per molecule of the formula

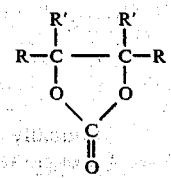

wherein R and R' are individually selected from the group consisting of alkyl groups having from 1 to 8 carbon atoms, aryl groups or lower alkyl or alkoxy, nitro or halogen substituted aryl groups, which comprises reacting in a liquid phase the corresponding alkylene iodohydrin having from 2 to 30 carbon atoms per molecule of the formula

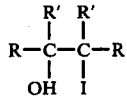

wherein R and R' are as defined above, with carbon dioxide at a temperature in the range of about 30° C. to 120° C. and at a total pressure between about atmospheric and 1400 psig, at a pH value of between 3 and 10, in the presence of oxygen or an oxygen-containing gas and an effective amount of a catalytic mixture of
(1) an iodide selected from the group consisting of potassium, sodium and lithium iodides and
(2) cupric carbonate dihydroxide, and recovering the desired alkylene carbonate.

2. A process according to claim 1 wherein the alkylene iodohydrin is selected from a group consisting of 1-iodo-2-ethanol, 1-iodo-2-propanol and 2-iodo-1-propanol.

3. A process according to claim 1 wherein the temperature is in the range of from about 70° C. to 100° C.

4. A process according to claim 1 wherein the total reaction pressure is between about 150 psig and 900 psig.

5. A process according to claim 1 wherein the reaction is carried out at a pH value of between 4 and 7.

6. A process according to claim 1 wherein the catalyst mixture is employed in the reaction in an amount between about 10 and 50 mole percent of the iodohydrin employed.

7. A process for the preparation of propylene carbonate which comprises reacting in the liquid phase an isomeric mixture of 1-iodo-2-propanol and 2-iodo-1-propanol with carbon dioxide at a partial pressure of between about 100 psig and 700 psig in the presence of oxygen at a partial pressure of between about 50 psig and 200 psig and an effective amount of a catalytic mixture of
(1) an iodide selected from the group consisting of potassium, sodium, and lithium iodides and
(2) cupric carbonate dihydroxide
at a temperature in the range of about 70° C. to 100° C. at a pH value of between 4 and 7, and recovering the desired propylene carbonate.

8. A process according to claim 7 wherein the iodide is potassium iodide.

9. A process for the preparation of alkylene carbonates having from 3 to 31 carbon atoms per molecule of the formula

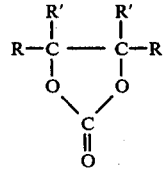

wherein R and R' are individually selected from the group consisting of alkyl groups having from 1 to 8 carbon atoms, aryl groups or lower alkyl or alkoxy, nitro or halogen substituted aryl groups, which comprises reacting in a liquid phase the corresponding alkylene iodohydrin having from 2 to 30 carbon atoms per molecule of the formula

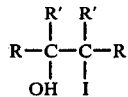

wherein R and R' are as defined above, with carbon dioxide at a temperature in the range of about 30° C. to 120° C. and at a total pressure between about atmospheric and 1400 psig, at a pH value of between 3 and 10, in the presence of oxygen or an oxygen-containing gas and an effective amount of a catalytic mixture of potassium iodide and cupric carbonate dihydroxide.

10. A process for the preparation of alkylene carbonates having from 3 to 31 carbon atoms per molecule of the formula

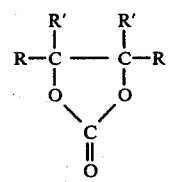

wherein R and R' are individually selected from the group consisting of alkyl groups having from 1 to 8 carbon atoms, aryl groups or lower alkyl or alkoxy, nitro or halogen substituted aryl groups, which comprises reacting in a liquid phase the corresponding alkylene iodohydrin having from 2 to 30 carbon atoms per molecule of the formula

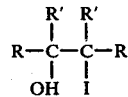

wherein R and R' are as defined above, with carbon dioxide at a temperature in the range of about 30° C. to 120° C. and at a total pressure between about atmospheric and 1400 psig, at a pH value of between 3 and 10, in the presence of oxygen or an oxygen-containing gas and an effective amount of a catalytic mixture of potassium iodide and calcium carbonate.

11. A process for the preparation of alkylene carbonates having from 3 to 31 carbon atoms per molecule of the formula

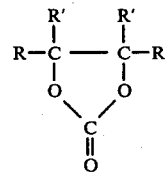

wherein R and R' are individually selected from the group consisting of alkyl groups having from 1 to 8 carbon atoms, aryl groups or lower alkyl or alkoxy, nitro or halogen substituted aryl groups, which comprises reacting in a liquid phase the corresponding alkylene iodohydrin having from 2 to 30 carbon atoms per molecule of the formula

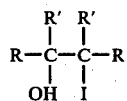

wherein R and R' are as defined above, with carbon dioxide at a temperature in the range of about 30° C. to 120° C. and at a total pressure between about atmospheric and 1400 psig, at a pH value of between 3 and 10, in the presence of oxygen or an oxygen-containing gas and an effective amount of a catalytic mixture of calcium iodide and zinc carbonate.

12. A process for the preparation of alkylene carbonates having from 3 to 31 carbon atoms per molecule of the formula

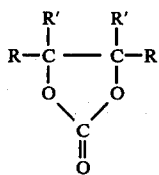

wherein R and R' are individually selected from the group consisting of alkyl groups having from 1 to 8 carbon atoms, aryl groups or lower alkyl or alkoxy, nitro or halogen substituted aryl groups, which comprises reacting in a liquid phase the corresponding alkylene iodohydrin having from 2 to 30 carbon atoms per molecule of the formula

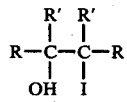

wherein R and R' are as defined above, with carbon dioxide at a temperature in the range of about 30° C. to 120° C. and at a total pressure between about atmospheric and 1400 psig, at a pH value of between 3 to 10, in the presence of oxygen or an oxygen-containing gas and an effective amount of a catalytic mixture of iron iodide and calcium carbonate.

13. A process for the preparation of alkylene carbonates having from 3 to 31 carbon atoms per molecule of the formula

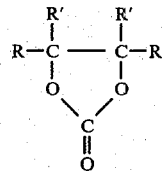

wherein R and R' are individually selected from the group consisting of alkyl groups having from 1 to 8 carbon atoms, aryl groups or lower alkyl or alkoxy, nitro or halogen substituted aryl groups, which comprises reacting in a liquid phase the corresponding alkylene iodohydrin having from 2 to 30 carbon atoms per molecule of the formula

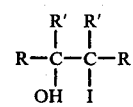

wherein R and R' are as defined above, with carbon dioxide at a temperature in the range of about 30° C. to 120° C. and at a total pressure between about atmospheric and 1400 psig, at a pH value of between 3 and 10, in the presence of oxygen or an oxygen-containing gas and an effective amount of a catalytic mixture of palladium iodide and calcium carbonate.

14. A process for the preparation of alkylene carbonates having from 3 to 31 carbon atoms per molecule of the formula

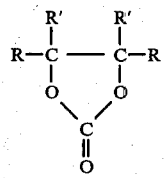

wherein R and R' are individually selected from the group consisting of alkyl groups having from 1 to 8 carbon atoms, aryl groups or lower alkyl or alkoxy, nitro or halogen substituted aryl groups, which comprises reacting in a liquid phase the corresponding alkylene iodohydrin having from 2 to 30 carbon atoms per molecule of the formula

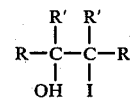

wherein R and R' are as defined above, with carbon dioxide at a temperature in the range of about 30° C. to 120° C. and at a total pressure between about atmospheric and 1400 psig, at a pH value of between 3 and 10, in the presence of oxygen or an oxygen-containing gas and an effective amount of a catalytic mixture of copper iodide and cupric carbonate dihydroxide.

* * * * *